(12) United States Patent
Allison

(10) Patent No.: US 9,956,038 B2
(45) Date of Patent: May 1, 2018

(54) RF OR MICROWAVE ABLATION CATHETER WITH REMOTE DICKE SWITCH

(71) Applicant: Coral Sand Beach LLC, Montclair, NJ (US)

(72) Inventor: Robert Allison, Rancho Palos Verdes, CA (US)

(73) Assignee: CORAL SAND BEACH LLC, Montclair, NJ (US)

( * ) Notice: Subject to any disclaimer, the term of this patent is extended or adjusted under 35 U.S.C. 154(b) by 71 days.

(21) Appl. No.: 15/128,142

(22) PCT Filed: Mar. 24, 2015

(86) PCT No.: PCT/US2015/022241
§ 371 (c)(1),
(2) Date: Sep. 22, 2016

(87) PCT Pub. No.: WO2015/148502
PCT Pub. Date: Oct. 1, 2015

(65) Prior Publication Data
US 2017/0105798 A1    Apr. 20, 2017

Related U.S. Application Data

(60) Provisional application No. 61/969,443, filed on Mar. 24, 2014.

(51) Int. Cl.
*A61B 18/18*    (2006.01)
*A61B 5/01*    (2006.01)
(Continued)

(52) U.S. Cl.
CPC ............ *A61B 18/1815* (2013.01); *A61B 5/01* (2013.01); *A61B 18/1206* (2013.01);
(Continued)

(58) Field of Classification Search
CPC . A61B 17/320068; A61B 18/02; A61B 18/14; A61B 18/1815; A61B 18/20; A61B 2018/00577; A61B 2018/00648; A61B 2018/00791; A61B 2018/00875; A61B 2018/00994; A61B 2562/06; A61B 5/01; A61B 5/0507; A61B 5/053; A61B 5/4836
See application file for complete search history.

(56) References Cited

U.S. PATENT DOCUMENTS

2007/0299488 A1    12/2007    Carr
2013/0237977 A1    9/2013    McCarthy et al.
2013/0281851 A1    10/2013    Carr

FOREIGN PATENT DOCUMENTS

WO    WO2008002517    1/2008

OTHER PUBLICATIONS

Supplementary European Search Report and Written Opinion in related EP Application 15767808.7, dated Nov. 13, 2017, 7 pages.
(Continued)

*Primary Examiner* — Daniel Fowler
(74) *Attorney, Agent, or Firm* — Wiggin and Dana LLP; Joseph Casino; Andrew D. Bochner

(57) ABSTRACT

The invention provides devices and systems, as well as associated methods of using them, that employ a remote Dicke switching element—i.e., distal to a radiometer. The devices, systems, and methods are suitable for both diagnostic and therapeutic applications in a wide variety of tissues.

12 Claims, 7 Drawing Sheets

(51) Int. Cl.
*A61B 18/12* (2006.01)
*A61B 18/14* (2006.01)
*G01J 5/08* (2006.01)
*G01K 11/00* (2006.01)
*G01K 13/00* (2006.01)
*A61B 18/00* (2006.01)
*G01J 5/00* (2006.01)

(52) U.S. Cl.
CPC ............ *A61B 18/1492* (2013.01); *G01J 5/08* (2013.01); *G01K 11/006* (2013.01); *G01K 13/002* (2013.01); *A61B 2018/00029* (2013.01); *A61B 2018/00351* (2013.01); *A61B 2018/00404* (2013.01); *A61B 2018/00434* (2013.01); *A61B 2018/00511* (2013.01); *A61B 2018/00577* (2013.01); *A61B 2018/00642* (2013.01); *A61B 2018/00755* (2013.01); *A61B 2018/00791* (2013.01); *A61B 2018/00875* (2013.01); *A61B 2018/00994* (2013.01); *A61B 2018/1823* (2013.01); *A61B 2018/1846* (2013.01); *A61B 2018/1861* (2013.01); *A61B 2218/002* (2013.01); *A61B 2562/0271* (2013.01); *G01J 2005/0081* (2013.01)

(56) References Cited

OTHER PUBLICATIONS

PCT International Search Report in PCT/US2015/022241, dated Jan. 10, 2015, 3 pages.
PCT Written Opinion of the International Searching Authority in PCT/US2015/022241, dated Jun. 29, 2015, 5 pages.
PCT International Preliminary Report on Patentability in PCT/US2015/022241, dated Sep. 27, 2016, 6 pages.

FIG. 3
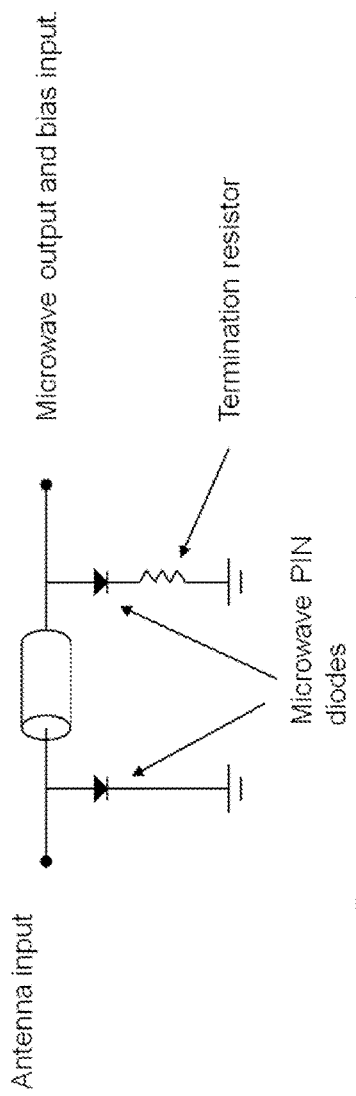
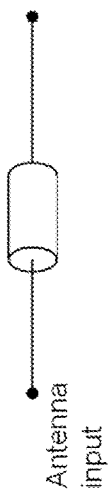

Coaxial In-line Diode Switch

RF OR MICROWAVE ABLATION CATHETER WITH REMOTE DICKE SWITCH

RELATED APPLICATION(S)

This application claims the benefit of U.S. Provisional Application No. 61/969,443, filed on Mar. 24, 2014.

The entire teachings of the above application(s) are incorporated herein by reference.

BACKGROUND OF THE INVENTION

Meaningful feedback of temperature or tissue characteristic state or change is critical to improving both safety and efficacy of catheter-based therapeutic ablation systems. Employing novel microwave radiometric sensing makes possible measurement of tissue characteristics and temperature at depth within a tissue target. In order to perform minimally invasive interventions, however, catheter cables are long and subject to varying temperatures caused by varying ambient temperature, temperature within the body, et cetera. As a result, a radiometric sensing system, with a radiometer at the proximal end and an antenna at the distal end will measure a combination of the desired tissue temperature and the temperature of the cable, diminishing the value of the intended application. Accordingly, a need exists for devices that overcome these limitations and associated methods of using them in ablation therapy.

SUMMARY OF THE INVENTION

The present invention answers these unmet needs by introducing a switch at or near the antenna, thereby mitigating the contribution of unknown temperature affects along the length of cable. Advantageously, the implementations provided by the invention allow introduction of an irrigation path along the length of cable through the switch and to antenna at distal end, which is a desirable feature, especially for radiofrequency (RF) ablation schemes.

In the case of a microwave (MW) ablation system, a similarly configured switch eliminates the temperature contributions from the cable in a similar way, a problem that is exacerbated in the MW system, since the microwave power heats the cable itself.

A diode switch has advantage of a continuous center conductor path out the antenna, including a cooling path in the RF case. The diodes also make the system suitable for handling high power delivery. Minor variations of the systems provided by the invention make them appropriate for integration to an RF or MW ablation solution. The present invention also provides, In some embodiments, a simple topology, with a single bias supply requiring no additional wires, just, for example, a coaxial cable (coax).

The present invention offers several advantages over existing modalities, including:

a) Improved accuracy/sensitivity of radiometric sensing by eliminating contribution of temperatures/influences along length of cable;

b) facilitating integration of radiometric sensing into long catheter systems, with improved accuracy;

c) accommodating use of a coolant path out to distal end of the catheter. A cooled tip catheter enhances performance of a system, such as an RF system, and mitigates risk of injury to the surface of the target tissue.

The remote Dicke switch scheme used in the present invention uses a single bias source and requires no conductors other than the coaxial center and outer conductors, although, In some embodiments, additional wires can be used. Both diodes in the switch are either ON or OFF at the same time—i.e., they are synchronized. Both diodes biased OFF results in a low loss path from the antenna to the radiometer. Both diodes biased ON blocks the antenna path and switches the termination resistor into the path to the radiometer. This is illustrated in FIGS. 3 and 4.

As already noted, a MW catheter is similar to a RF ablation catheter except microwave power will be conducted down the coax to the antenna. The diode switch must handle the microwave power. Accordingly, the microwave generator must be off during the reference termination period of the radiometer measurement otherwise, the termination resistor will absorb all of the generator power. The diodes must have sufficient back bias (28V) to prevent rectification of the high power microwave signal during ablation and the multiplexer must include a microwave generator input. The microwave ablation power heats the long, small diameter coaxial catheter. The remote switching scheme eliminates cable heating from the temperature measurement. Since temperature measurement is interleaved with microwave ablation, the delivered average power is reduced by the measurement time. In certain embodiments, temperature measurement occurs over 60, 55, 50, 45, 40, 35, 30, 25, 20, 15, 10, 5%, or less, of the time of the ablation procedure to maximize delivered power. In particular embodiments, temperature measurement is over less than half of the ablation time.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 3A-C provides diagrams of an exemplary Remote (Dicke) Switch Schematic (3A), and exemplary equivalent circuit diagrams of the switch in the off (3B) and on (3C) positions. In FIG. 3B, back biased, the diodes are very small capacitors and are effectively not present leaving just a transmission line through path. In FIG. 3C, forward biased, the diodes are very small resistors. The termination resistor is connected between center and outer conductors. The second diode shorts the quarter wavelength coax section to ground creating an open circuit at the termination resistor. The switch becomes just a resistor to ground.

DETAILED DESCRIPTION OF THE INVENTION

Figure 1:
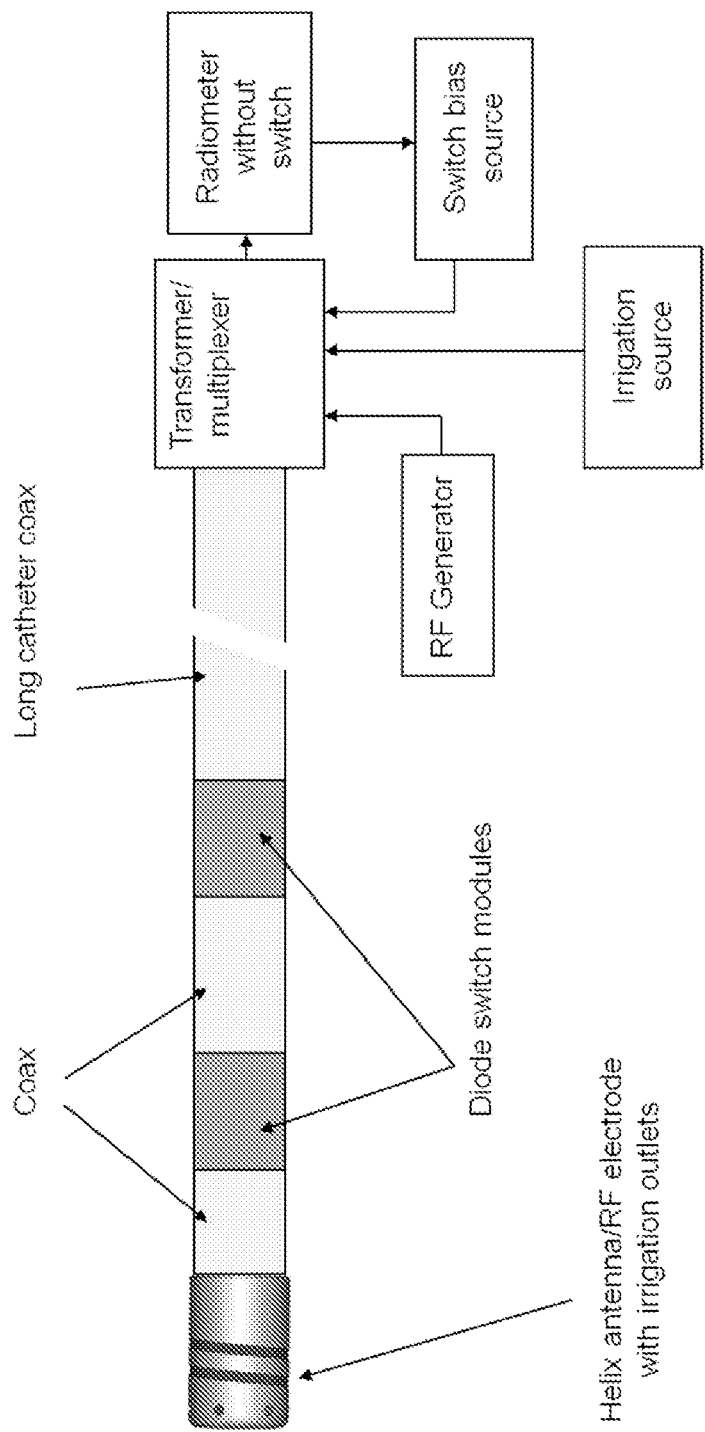
FIG. 1 is a diagram of an exemplary RF Ablation Catheter with Remote Dicke Switch.
Figure 2:
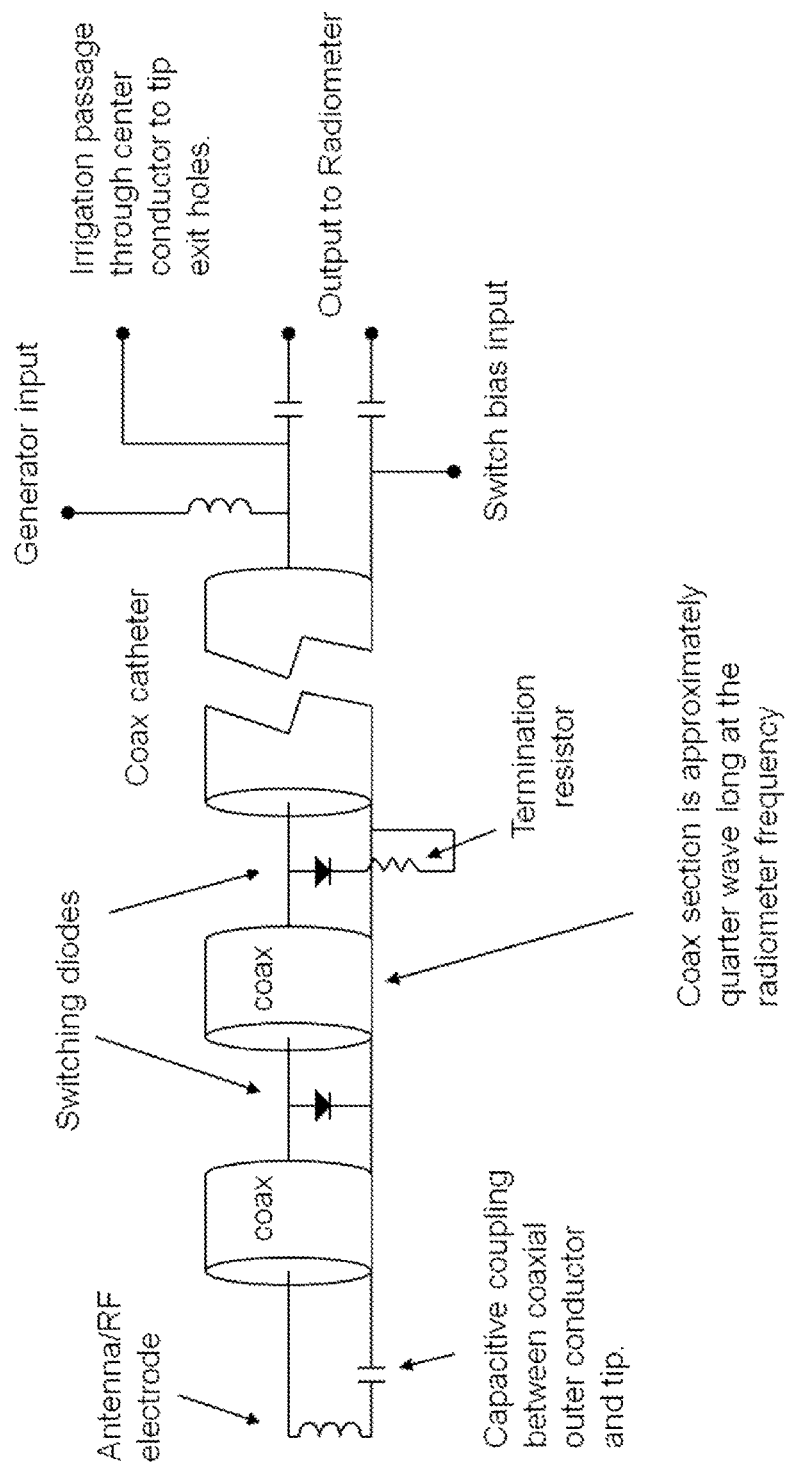
FIG. 2 is a diagram of a Low Frequency Equivalent Circuit to that depicted in FIG. 1.
Figure 4:
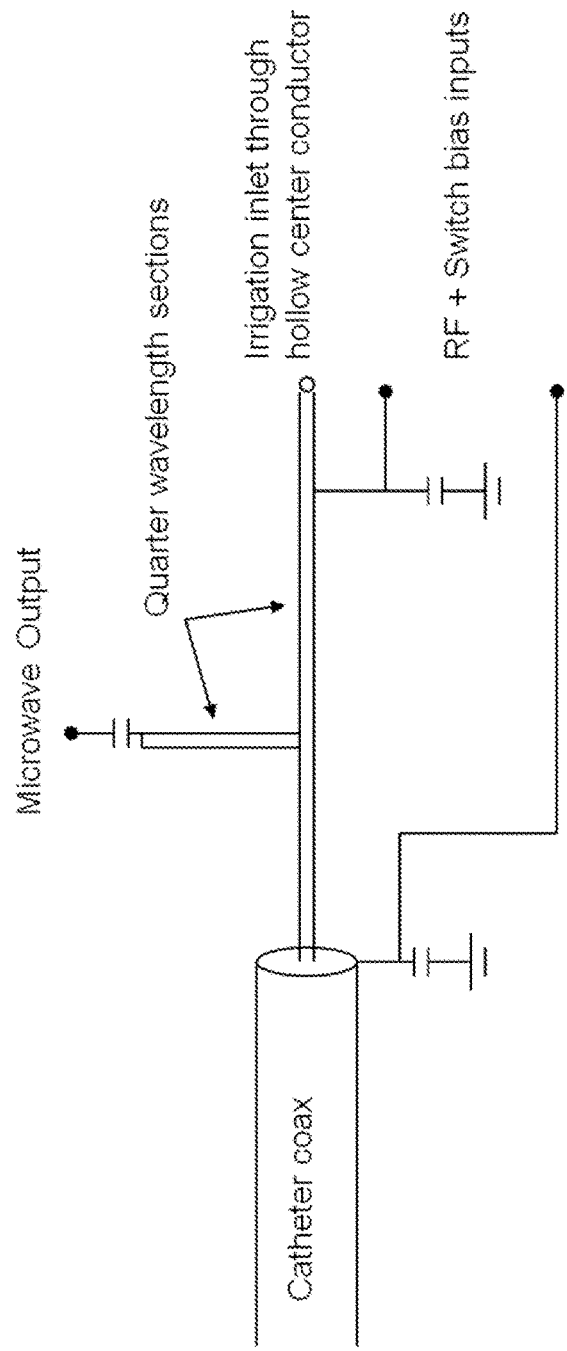
FIG. 4 is a diagram of an exemplary transformer/multiplexer scheme. In some embodiments, a low impedance coaxial cable is used to reduce losses. An impedance transformation from the low coax impedance to a 50 ohm output impedance can be accomplished, in some embodiments, by adjusting the impedance of the quarter wavelength sections.
Figure 5:
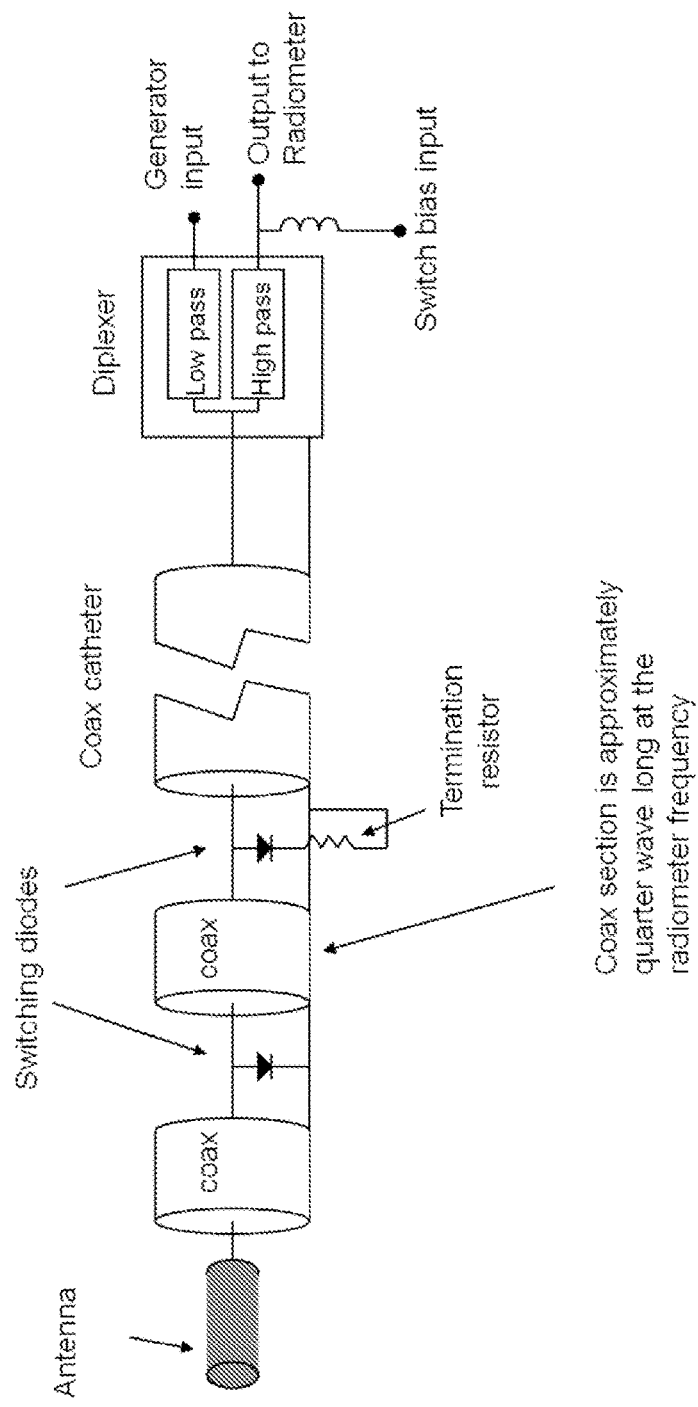
FIG. 5 is a block diagram of an exemplary microwave-based system with a remote Dicke switch.
Figure 6:
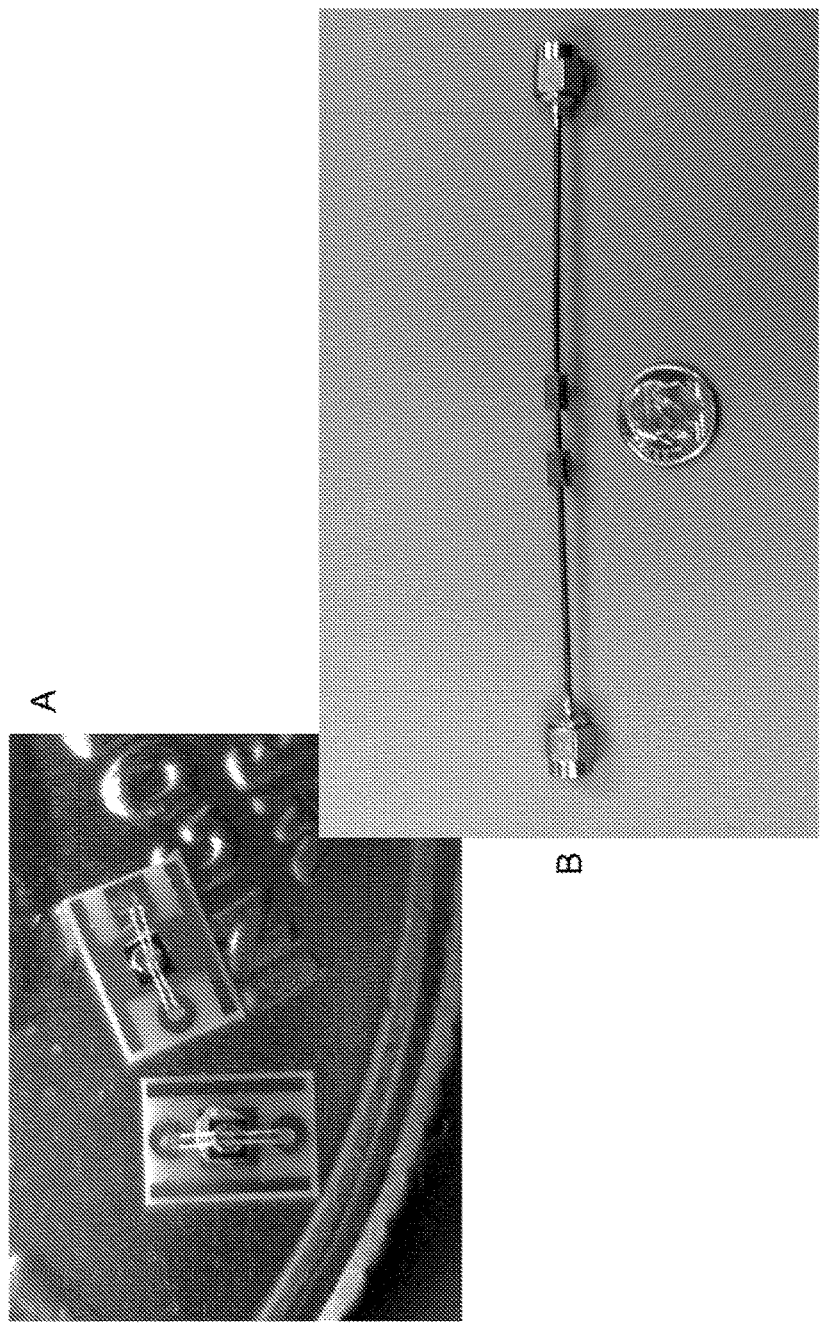
FIGS. 6A and 6B provide a pair of micrographs showing a diode switch test circuit (6A) with PIN diodes on alumina mounts and two diode modules attached to 0.047" coax (6B; diode modules were made rectangular for ease of test circuit assembly).
Figure 7:
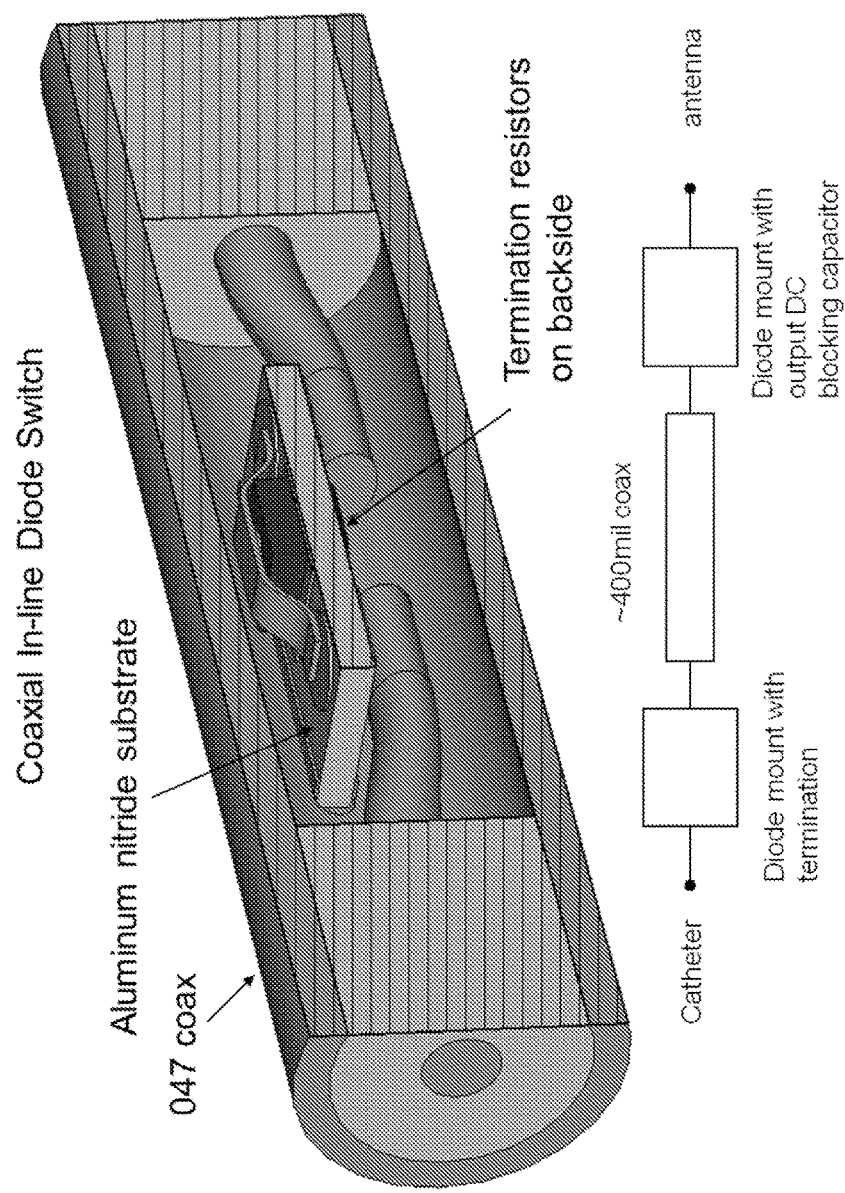
FIG. 7 shows a representation and block diagram of a co-axial inline diode switch that can be used in embodiments of the present invention.

A description of example embodiments of the invention follows.

The invention provides devices and systems, as well as associated methods of using them, that employ a remote Dicke switching element. The devices, systems, and methods are suitable for both diagnostic and therapeutic applications in a wide variety of tissues.

Accordingly, in a first aspect, the invention provides an ablation system comprising:
 a) a coaxial cable having a first end and a second end;
 b) a microwave antenna coupled to the first end of the coaxial cable;
 c) a Dicke switch proximate to the antenna, the Dicke switch coupled to and between, the antenna and coaxial cable; and
 d) a multiplexer coupled to the second end of the coaxial cable, the multiplexer being between, and coupled to, the coaxial cable and: an ablation energy generator, a switch bias source, and radiometer, the radiometer being configured to measure temperature from the antenna, the radiometer coupled to a control of the ablation energy generator.

A "Dicke switch" is the front end switch in a radiometer, and switches between the antenna input and a reference termination of known temperature at a somewhat rapid rate (e.g., about 100-10,000 KHZ, 50% duty). The result is a radiometer whose output is a voltage proportional to the temperature different between the antenna input and the reference temperature. The advantage is that all components downstream of the switch are common to both measurement paths and subtract out of the output voltage. The radiometer is much more stable than schemes without the switch, less prone to drifts and other errors caused by imperfections in the radiometer electronics. In some embodiments, the Dicke switch comprises a first switching diode module, a second switching diode module, the first and second switching diode modules being synchronized and coupled to a bias source, a segment of coaxial cable being between, and coupled to, the switching diode modules, the segment of coaxial cable being a length of about a quarter wavelength at a radiometer sensing frequency (such as 4.0 GHz+/−200 MHz), and the second switching diode module (i.e., the module furthest from the antenna) being coupled to a termination resistor. In particular embodiments, the diodes in the switching diode modules are microwave PIN diodes. The diodes of the switching diode modules, when in the off position, are back-biased, effectively acting as small capacitors. This forms a direct path from the antenna to the coaxial catheter and radiometer. When in the on position, the diodes of the switching modules are forward-biased, effectively acting as very small resistors. The second diode shorts the approximately quarter wavelength coaxial cable to ground, blocking signal from the antenna and creating a microwave open circuit at the first diode which has switched in the termination resistor from the coaxial center conductor to the outer conductor. This is the reference termination half of the radiometer measurement.

An "ablation energy generator" is an electronic device that provides the energy for ablation, e.g., when coupled to a suitable antenna. Exemplary ablation energy generators include microwave transducers and radiofrequency electrodes. A variety of suitable antennas can be used by the skilled artisan, including either omnidirectional or directional antennas (including, for example, omnidirectional antennas that are partially shielded). Antennas can be permanently fixed to a device or system provided by the invention, or may be disposable or otherwise easily replaceable. The length of the coaxial cable can be adjusted to a length suitable for any particular application. In particular embodiments, the cable is from about 70 to about 160 cm, e.g., about: 50, 60, 70, 80, 90, 100, 110, 120, 130, 140, 150, 160, 170, 180, 190, 200 cm, or more. In other embodiments, the length of the coaxial cable is less than about 50 cm. The diameter of the coaxial cable and/or antenna may be about 0.75 to about 3.0 mm, e.g., about 0.8, 0.9, 1.0, 1.1, 1.2, 1.3, 1.4, 1.5, 1.6, 1.7, 1.8, 1.9, or 2.0 mm. In some embodiments, the coax is a low impedance coaxial cable. In other embodiments, it is an about 50 ohm output impedance. In some embodiments, a device or system provide by the invention provides an impedance transformation.

"Coupled", as in, e.g., the multiplexer and/or radiometer are coupled to the coaxial cable, refers to a communicative coupling that facilitates the effective transfer of electrical signals and encompasses wireless as well as physically wired connections, such as wires and cables, such as coaxial cables. A "control", as in a control of the ablation energy generator, is a circuitry that facilitates modulating the intensity and/or frequency of the ablation energy generator. For example, a control of the ablation energy generator (such as a microwave energy generator) can increase or decrease the frequency, intensity, or frequency and intensity of the energy emitted from the ablation energy generator. Accordingly, a coupling of, e.g., the radiometer to a control of the ablation energy generator produces a feedback system that effectively controls the ablation process. The controls of the ablation energy generator can be separate controls or a single control that integrates multiple signals.

Any suitable radiometer can be used consonant with the invention. In particular embodiments, the radiometer is a Dicke radiometer. Exemplary radiometers are also described in U.S. Pat. Nos. 6,496,738 and 6,210,367, which are incorporated by reference in their entirety. The devices (such as radiometers) described herein and in the above patents can be configured on a single integrated circuit. Such integrated circuits can further comprise elements described in the system provided by the invention, such as an ablation energy generator, circuitry for measuring impedance mismatch, and additional elements, such as those illustrated in the figures or otherwise described herein.

Microwave frequencies are typically used for detection of temperature and, in some embodiments, impedance, in the present invention (e.g., at a sensing frequency), including microwave energy from about 1 to about 30 GHz, e.g., about 1-5 GHz, more particularly, about 3-5 GHz, and, still more particularly, about 4 GHz, e.g., 4 GHz+/−200 MHz In some embodiments, microwaves are the ablation means used for heating, e.g., at a heating frequency, where the heating frequency is different from the sensing frequency. A heating frequency can also be used for measuring an impedance mismatch. Exemplary heating frequencies, in particular embodiments, are about: 2.5 GHz (e.g. about 2.45 to about 2.55 GHz), 900 MHz (e.g., about 850 to about 950 MHz), or for shallower tissue heating, such as surface heating, about 10-20 GHz. Suitable frequencies can be selected by the skilled artisan based on well-understood principles, e.g., the scanning depth in a target sample, e.g., a tissue, and associated parameters, such as antenna size relative to the application (e.g., for use in an adult versus a neonate) on a body. Multiple frequencies can be used, e.g., both for sensing and, in certain embodiments, ablation. For example, to monitor temperature and/or impedance mismatch 1, 2, 3, 4, 5, or more different frequencies (or bandwidths) can be used. Similarly, where microwave or radio frequencies are used for ablation, 1, 2, 3, 4, 5, or more different frequencies (or bandwidths) can be used to apply energy.

In some embodiments, the ablation energy generator is a radiofrequency generator. Exemplary frequencies for RF ablation are about 500 KHZ, e.g., about 300, 400, 500, 600, or 700 KHZ. In these embodiments, the antenna further includes a radiofrequency electrode, e.g., wrapped around the MF antenna, and the system further includes a capacitive coupling between the electrode and coaxial outer conductor.

In certain embodiments, a system provided by the invention includes a path for cooling fluid (such as an aqueous buffer, such as saline, or other fluid suitable or use in an ablation process) passing from and through the coaxial cable and the microwave antenna, the antenna comprising one or more outlets for the cooling fluid. In some embodiments, the system further includes a control for an irrigation means coupled to the multiplexer, distal to the coaxial cable, the control of the irrigation means coupled to the radiometer.

In other embodiments, the ablation energy generator is a microwave frequency generator. In more particular embodiments, the microwave frequency generator is operating at about 2.5 GHz.

The systems and devices provided by the invention may further include circuitry for measuring impedance mismatch, the circuitry coupled to a control of the ablation energy generator.

The devices and systems provided by the invention can further comprise a user-readable output. In particular embodiments, the user-readable output provides a user-readable display of one or both of: a tissue temperature and an impedance mismatch.

In some embodiments, the systems and devices provided by the invention may include a closed power source.

In certain embodiments, the devices and systems provided by the invention include a non-transient storage medium for recording the measured temperature and/or impedance mismatch.

In some embodiments, the devices and systems provided by the invention include a non-transient storage medium with reference values of temperature and/or impedance mismatch stored thereon, the reference values being suitable for measuring temperature and/or characterizing a biological tissue, including in a healthy, compressed (e.g., as a measure of device depth in the tissue), or diseased (e.g., plaqued/occluded (e.g., atherosclerotic), burnt, scarred, cirrhotic, or cancerous) state.

In certain embodiments, the antenna of the devices or systems provided by the invention are proximate to, or are in contact with, a biological tissue. In certain embodiments, the biological tissue is of a mammal, such as a human. In some embodiments, the biological tissue is in need of ablation therapy.

In a related aspect, the invention provides both diagnostic and therapeutic methods using the devices and systems provided by the invention. In some embodiments, the methods entail placing the antenna of a device or system provided by the invention proximate to, or in contact with, a biological tissue in need of ablation, and activating the ablation energy generator, thereby ablating the biological tissue. In some embodiments, the methods include measuring the temperature (and optionally impedance mismatch) of the biological tissue substantially concurrently with activating the ablation energy generator. Particularized, non-limiting examples of applications of these methods include renal denervation, tumor ablation, carotid body modulation, and cardiac ablation.

It should be understood that for all numerical bounds describing some parameter in this application, such as "about," "at least," "less than," and "more than," the description also necessarily encompasses any range bounded by the recited values. Accordingly, for example, the description "at least 1, 2, 3, 4, or 5" also describes, inter alia, the ranges 1-2, 1-3, 1-4, 1-5, 2-3, 2-4, 2-5, 3-4, 3-5, and 4-5, et cetera.

Headings used in this application are for convenience only and do not affect the interpretation of this application.

Preferred features of each of the aspects provided by the invention are applicable to all of the other aspects of the invention mutatis mutandis and, without limitation, are exemplified by the dependent claims and also encompass combinations and permutations of individual features (e.g., elements, including numerical ranges and exemplary embodiments) of particular embodiments and aspects of the invention, including the working examples. For example, particular experimental parameters exemplified in the working examples can be adapted for use in the claimed invention piecemeal without departing from the invention. For example, for materials that are disclosed, while specific reference of each of the various individual and collective combinations and permutations of these compounds may not be explicitly disclosed, each is specifically contemplated and described herein. Thus, if a class of elements A, B, and C are disclosed as well as a class of elements D, E, and F and an example of a combination of elements A-D is disclosed, then, even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-groups of A-E, B-F, and C-E are specifically contemplated and should be considered disclosed from disclosure of A, B, and C; D, E, and F; and the example combination A-D. This concept applies to all aspects of this application, including elements of a composition of matter and steps of method of making or using the compositions.

The forgoing aspects of the invention, as recognized by the person having ordinary skill in the art following the teachings of the specification, can be claimed in any combination or permutation to the extent that they are novel and non-obvious over the prior art—thus, to the extent an element is described in one or more references known to the person having ordinary skill in the art, they may be excluded from the claimed invention by, inter alia, a negative proviso or disclaimer of the feature or combination of features.

It should be understood that the example embodiments described above may be implemented in many different ways. In some instances, the various methods and machines described herein may be implemented by a physical, virtual, or hybrid general purpose computer, or a computer network environment.

Embodiments or aspects thereof may be implemented in the form of hardware, firmware, or software. If implemented in software, the software may be stored on any non-transient computer-readable medium that is configured to enable a processor to load the software or subsets of instructions thereof. The processor then executes the instructions and is configured to operate or cause an apparatus to operate in a manner as described herein.

Further, firmware, software, routines, or instructions may be described herein as performing certain actions and/or functions of the data processors. However, it should be appreciated that such descriptions contained herein are merely for convenience and that such actions, in fact, result from computer devices, processors, controllers, or other devices executing the firmware, software, routines, instructions, etc.

It should also be understood that the schematics may include more or fewer elements, be arranged differently, or be represented differently. But it should further be understood that certain implementation may dictate that the schematic be implemented in a particular way.

While this invention has been particularly shown and described with references to example embodiments thereof, it will be understood by those skilled in the art that various changes in form and details may be made therein without departing from the scope of the invention encompassed by the appended claims.

What is claimed is:

1. An ablation system comprising:
    a coaxial cable having a first end, a second end, an inner conductor and an outer conductor;
    a microwave antenna coupled to the first end of the coaxial cable;
    a Dicke switch proximate to the antenna, the Dicke switch coupled to the antenna and coaxial cable, the Dicke switch located between the antenna and coaxial cable, the Dicke switch comprising two diode switches, the diode switches located between the inner conductor and outer conductor;
    a multiplexer coupled to the second end of the coaxial cable, the multiplexer being coupled to the coaxial cable;
    an ablation energy generator, a switch bias source, and radiometer, the radiometer being configured to measure temperature from the antenna, the radiometer coupled to a control of the ablation energy generator; and
    circuitry for measuring impedance mismatch, the circuitry coupled to a control of the ablation energy generator.

2. The system of claim 1, wherein the ablation energy generator is a radiofrequency generator, the antenna further comprising a radiofrequency electrode and a capacitive coupling between the electrode and coaxial outer conductor.

3. The system of claim 2, further comprising a path for cooling fluid passing from and through the coaxial cable and the microwave antenna, the antenna comprising one or more outlets for the cooling fluid.

4. The system of claim 3, further comprising a control of an irrigation source coupled to the multiplexer, distal to the coaxial cable, the control of the irrigation source coupled to the radiometer.

5. The system of claim 1, wherein the ablation energy generator is a microwave frequency generator.

6. The system of claim 5, wherein the microwave frequency generator is configured to operate at about 2.5 GHz.

7. The system of claim 1, wherein the system further comprises a user-readable output.

8. The system of claim 7, wherein the user-readable output provides a user-readable display of one or both of a tissue temperature and an impedance mismatch.

9. The system of claim 1, wherein the system comprises a non-transient storage medium for recording the measured temperature and/or impedance mismatch.

10. The system of claim 1, wherein the ablation energy generator is configured to perform ablation, wherein the ablation is performed simultaneously with the temperature measurement via the radiometer.

11. A method of ablating a biological tissue in need thereof, comprising the steps of:
    placing a microwave antenna of an ablation system proximate to, or in contact with, the biological tissue, wherein the system includes:
    a coaxial cable having a first end, a second end, an inner conductor and an outer conductor;
    the microwave antenna coupled to the first end of the coaxial cable;
    a Dicke switch proximate to the antenna, the Dicke switch coupled to the antenna and coaxial cable, the Dicke switch located between the antenna and coaxial cable, the Dicke switch comprising two diode switches, the diode switches located between the inner conductor and outer conductor;
    a multiplexer coupled to the second end of the coaxial cable, the multiplexer being coupled to the coaxial cable;
    an ablation energy generator, a switch bias source, and radiometer, the radiometer being configured to measure temperature from the antenna, the radiometer coupled to a control of the ablation energy generator; and
    circuitry for measuring impedance mismatch, the circuitry coupled to a control of the ablation energy generator, wherein activating the ablation energy generator thereby ablates the biological tissue.

12. The method of claim 11, further comprising the step of measuring the temperature of the biological tissue and/or impedance mismatch substantially concurrently with activating the ablation energy generator.

* * * * *